United States Patent [19]

Sugiura et al.

[11] 4,280,992

[45] Jul. 28, 1981

[54] IMMUNOLOGICALLY ACTIVE SUBSTANCE-GLASS CONJUGATES, PROCESS FOR PRODUCING THE SAME AND DIAGNOSTIC REAGENTS CONTAINING THE SAME

[75] Inventors: Masakuzu Sugiura, Nara; Junichiro Kikutake, Osaka; Masaru Yoshida; Shigeharu Kondo, both of Kyoto, all of Japan

[73] Assignee: Sanyo Chemical Industries, Ltd., Kyoto, Japan

[21] Appl. No.: 5,856

[22] Filed: Jan. 23, 1979

[30] Foreign Application Priority Data

Feb. 14, 1978 [JP] Japan ................................. 53-16342

[51] Int. Cl.³ ...................... G01N 33/48; G01T 1/00
[52] U.S. Cl. ..................................... 424/1; 23/230 B; 424/12; 435/7
[58] Field of Search .................... 424/1, 12; 23/230 B; 435/7

[56] References Cited

U.S. PATENT DOCUMENTS

| 3,652,761 | 3/1972 | Weetall | 424/12 |
| 3,975,511 | 8/1976 | Vann et al. | 424/12 |
| 4,059,685 | 11/1977 | Johnson | 424/12 |
| 4,108,975 | 8/1978 | Hales | 424/1 |

OTHER PUBLICATIONS

Hamaguchi et al., Eur. J. Biochem, 71 (1976), pp. 459-467.

Primary Examiner—Benjamin R. Padgett
Assistant Examiner—Christine M. Nucker
Attorney, Agent, or Firm—Oblon, Fisher, Spivak, McClelland & Maier

[57] ABSTRACT

An immunologically active substance-glass conjugate comprising an immunologically active substance physically or chemically bound to the surface of a frosted glass makes it possible to assay physiologically active substances in body fluids with high sensitivity.

35 Claims, 2 Drawing Figures

IMMUNOLOGICALLY ACTIVE SUBSTANCE-GLASS CONJUGATES, PROCESS FOR PRODUCING THE SAME AND DIAGNOSTIC REAGENTS CONTAINING THE SAME

BACKGROUND OF THE INVENTION

1. Field of the Invention

This invention relates to immunologically active substance-glass conjugates, process for producing the same, and diagnostic reagents containing the same and process for assaying physiologically active substances using the same. More particularly, it relates to immunologically active substance-frosted glass conjugates suited for use in assaying with very high sensitivity physiologically active substances in body fluids, such as hormones and proteins, process for producing the same, diagnostic reagents containing the same and process for assaying physiologically active substances using the same.

2. Description of the Prior Art

Assaying of physiologically active substances (such as hormones and proteins) contained in body fluids (such as urine, serum), is important from the diagnostic point of view, and can be carried out either by radioimmunoassay (hereinafter abbreviated to RIA) or by enzyme-immunoassay (hereinafter abbreviated to EIA). Both RIA and EIA are based on the same principle, namely specificity of antigen-antibody reactions.

Useful assaying systems commonly used for RIA and EIA are solid phase systems using insolubilized immunologically active substances with the aid of water-insoluble carriers. Water-insoluble carriers so far used are (1) plastics such as polystyrene and polyethylene, (2) natural polymers such as sepharose and cellulose, (3) glasses, and so on. Use of plastics (such as polystyrene and polyethylene) as the water-insoluble carriers is disadvantageous, because storage stability and assay precision are unsatisfactory. Immunologically active substances bound to natural polymers such as sepharose and cellulose are flocculent or fluffy, and difficult to treat and require a skill in assaying therewith. On the other hand, glasses are different from the above-mentioned water-insoluble carriers in that immunologically active substances can be bound to them through covalent bonds and that immunologically active substances bound to glasses are stable and can be handled very easily. These products, however, still suffer from disadvantages in that quantity of an immunologically active substance that can be bound to a glass is small and therefore sensitivity and precision are not fully satisfactory and assay range is rather narrow.

SUMMARY OF THE INVENTION

Under these circumstances, the inventors have made extensive researches to eliminate the above drawbacks in those prior arts and finally accomplished the present invention.

Accordingly, it is an object of this invention to provide immunologically active substance-glass conjugates which bring very high sensitivity and precision in assaying therewith physiologically active substances in body fluids, process for producing the same, and diagnostic reagents containing the same.

It is another object of the invention to provide immunologically active substance-glass conjugates which make it possible to assay physiologically active substances in body fluids in a broader range, process for producing the same and diagnostic reagents containing the same.

It is still another object of the invention to provide process for assaying physiologically active substances in body fluids with high sensitivity and precision using immunologically active substance-glass conjugates.

Briefly, these and further objects of the invention as will hereinafter become more readily apparent have been attained broadly by providing immunologically active substance-glass conjugates comprising immunologically active compounds or substances physically or chemically bound to the surface of a frosted glass, methods of producing the same, diagnostic reagents containing the same and process for assaying physiologically active substances in body fluids using the same.

BRIEF DESCRIPTION OF THE DRAWING

In describing this invention, reference shall be made to the accompanying drawings, in which.

DETAILED DESCRIPTION OF THE PREFERRED EMBODIMENTS

Figure 1:
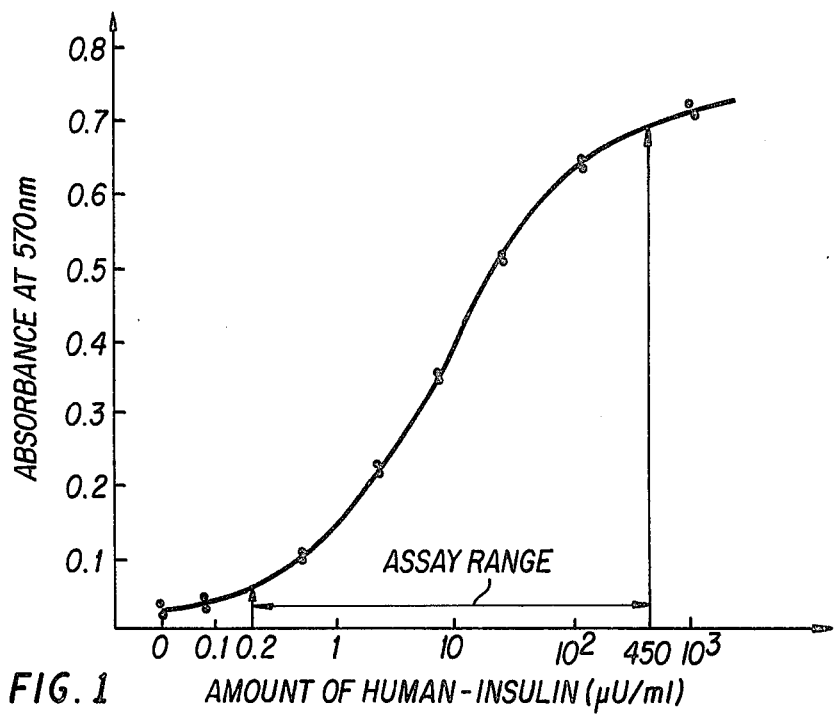
FIG. 1 is a standard curve for assaying human insulin by sandwich EIA method (cf. Example 3)

The immunologically active substance to be used in the present invention is not particularly critical. Suitable ones include antigens and antibodies. Illustrative examples of antigents are hormones, such as insulin, gonadotropin, 17-ketosteroids, growth hormone, thyroxine, triiodothyronine and thyroid stimulating hormone; proteins, such as IgG, IgA, IgM, IgE, α-fetoprotein, CEA (carcinoembryonic antigen) and protamines; and antigenic component of pathogens such as pathogenic bacteria (for example streptococci), viruses (for example hepatitis virus and rubella virus), protozoa (for example toxoplasma gondii and malarial parasites) and the like. Suitable antibodies include, for example, antisera obtainable in a conventional manner by immunizing mammals (such as rabbits and goats) with the above-mentioned antigens. Preferably, the antibodies are the ones obtained from the antisera by conventional purification methods such as fractionation using saturated ammonium sulfate, DEAE-cellulose column chromatography and affinity chromatography.

The frosted glass to be used in this invention is not particularly critical. There can be used, for example, physically (mechanically) frosted glasses and chemically frosted glasses described in Encyclopedia chimica, vol. 5, page 999 (Kyoritsu Publishing Co., 1963). Generally, those glasses that have an irregularly and minutely uneven surface caused by a physical or chemical treatment are used. Suitable physical treatment is, for example, abrading the glass surface using an abrasive material (e.g. abrasive, abrasive paper, abrasive-coated textile), spraying an abrasive material (e.g. emery) by the aid of compressed air onto the glass surface (sandblast), or abrading the glass surface with an abrasive material in a ball mill, for instance. Suitable chemical treatment is, for example, etching with hydrofluoric acid, ammonium fluoride or an alkali. Considering processability and efficiency in frosting, the sandblast method and the method using a frosting solution containing hydrofluoric acid or ammonium fluoride are preferred among physical and chemical methods, respectively. Shapes of glass bodies are not critical, but suitable shapes include cylindrical, spherical tubular and cubic. Size of the glass bodies is not paticulary critical, but the maximum diameter is usually 1 to 20 mm and the minimum diameter is usually 1 mm or more.

Suitable frosted glasses include those having a frosting-degree of generally 1.5 to 10.0, preferably 2.0 to 9.0. In this invention, the frosting-degree is defined as a ratio of enzyme activity of an enzyme bound to frosted glass to that of an enzyme bound to unfrosted glass (having same shape and size). In the above, the enzyme activities are determined by the following method:

(i) Preparation of Enzyme glass conjugates

Equal amounts of the frosted glass and the unfrosted glass having the same shape and size as those of the frosted glass are immersed in 10% solution of γ-aminopropyl-triethoxysilane in acetone. After incubation at 25° C. for an hour, these glasses are filtered off and washed with deionized water. To these treated glasses, there is added 20% aqueous solution of glutaraldehyde. After standing at 25° C. for an hour, the glasses are washed with deionized water. The glasses so treated are then immersed in 0.5 mg/ml aqueous solution of glucose oxidaze (GOD) (enzyme activity of 34.0U/mg, Toyo Boseki K.K.). After incubation at 25° C. for an hour and then at 4° C. for 15 hours, the glasses are filtered off and washed with deionized water to obtain GOD-frosted glass conjugate and GOD-unfrosted glass conjugate for measuring absorbance.

(ii) Measurement of Absorbance

A certain number (usually one piece) of the GOD-frosted glass conjugate is put into each of ten test tubes. An enzyme substrate solution containing β-D-glucose is added into each tube and then a color former solution containing 3-methyl-2-benzothiazolinonehydrazone hydrochloride (MBTH), N,N-diethylaniline (DEA) and peroxidase (POD) are added thereto. After incubation, the absorbances at 590 n m of supernatants in each test tube are measured. The above procedure is repeated except that the GOD-unfrosted glass conjugate is used instead of the GOD-frosted glass conjugate.

An average of the absorbances at 590 nm of supernatants in each test tube is estimated as the enzyme activity of the enzyme-frosted glass conjugate or enzyme-unfrosted glass conjugate, respectively.

The frosting-degree of the frosted glass(x) is calculated from the following equation (1).

$$X = \frac{\text{the enzyme activity of the enzyme bound to the frosted glass}}{\text{the enzyme activity of the enzyme bound to the unfrosted glass}} \quad (1)$$

The weight ratio of the immunologically active substance to the frosted glass to be used is not especially critical, but can be varied within a wide range according to requirements. For example, 10 to 1000 parts, preferably 50 to 300 parts, of a solution of the immunologically active substance is used per 100 parts of the frosted glass, the concentration of the solution being usually 0.001 to 40 g/100 ml preferably 0.01 to 0.1 g/100 ml.

According to the invention, it is essential to use a specific carrier, that is a frosted glass, for insolubilizing the immunologically active substance. Methods of binding the immunologically active substance to the frosted glass are not particularly critical. The immunologically active substance may be bound to the frosted glass surface by physical or chemical methods. The latters are preferred in view of binding a large amount of the immunologically active substance to the frosted glass firmly and permanently.

Binding by a physical method can be attained mainly by physical adsorption (van der Waals adsorption). Thus, the frosted glass may be dipped in a solution of the immunologically active substance and incubated, or allowed to stand, for an appropriate period of time to form physical binding. The solution can have a concentration of generally 0.001 to 40 g/100 ml preferably 0.01 to 0.1 g/100 ml. The dipping or immersion treatment can be carried out, for example, at a temperature of 0° to 45° C. for 1 to 48 hours.

As a suitable chemical method, there can be mentioned a method which comprises binding the immnologically active substance to the frosted glass surface with the aid of a silane coupling agent and if necessary a cross-linking agent.

There may be used any silane coupling agent having in its molecule both a functional group reactive with the frosted glass and a functional group reactive with the immunologically active substance and/or the cross-linking agent. Examples of suitable functional groups reactive with the frosted glass include those reactive with a silanol group of the frosted glass; and include, for example, alkoxysilyl groups (such as methoxy- or ethoxy-substituted sylyl groups), halosilyl groups (such as chloro-substituted silyl groups), and the like. Examples of suitable functional groups reactive with the immunologically active substance and/or the crosslinking agent are those reactive with amino, carboxyl and/or thiol group(s); and include, for instance, carboxyl, epoxy, haloalkyl (such as chloroethyl and chloropropyl), aldehyde, amino (primary and secondary amino), thiol, isocyanate, carboxylate, imino and nitrile (or cyano) groups, and the like. More specifically, examples of suitable functional groups reactive with the amino group are carboxyl, epoxy, haloalkyl and aldehyde groups; suitable functional groups reactive with the carboxyl group include, for example, amino (primary and secondary amino) and epoxy groups; and suitable functional groups reactive with the thiol group include thiol, epoxy, haloalkyl and aldehyde groups, and the like. Illustrative examples of suitable silane coupling agents are:

(1) Silane coupling agents containing amino and alkoxysilyl groups: aminoalkyl-trialkoxysilanes (such as γ-aminopropyl-trimethoxysilane, γ-aminopropyl-triethoxysilane), N-(β-aminoethyl)-γ-aminopropyl-methyl-dimethoxysilane, N-(β-aminoethyl)-γ-aminopropyl-trimethoxysilane, and the like;

(2) Silane coupling agents containing thiol and alkoxysilyl groups: mercaptoalkyl-trialkoxysilanes (such as γ-mercoptopropyl-trimethoxysilane), and the like;

(3) Silane coupling agents containing epoxy and alkoxysilyl groups: γ-glycidoxypropyl-trimethoxysilane, triethoxysilylmethyl-ethylene oxide, β-(3,4-epoxycyclohexyl)ethyl-trimethoxysilane, and the like.

(4) Silane coupling agents containing carboxyl and alkoxysilyl groups: 2-(trimethoxysilyl)propionic acid, and the like; and (5) Silane coupling agents containing haloalkyl and alkoxysilyl groups: γ-chloropropyl-trimethoxysilane, and the like.

In binding the immunologically active substances to the frosted glass, the silane coupling agent may be used with or without the crosslinking agent.

The crosslinking agent may be selected according to the kind of the silane coupling agent and the kind of the immunologically active substance to be bound. There may be used any crosslinking agent which can crosslink the silane coupling agent with the immunologically active substance: As such crosslinking agents there may be mentioned those compounds that can crosslink the amino, carboxyl or thiol group of the silane coupling agent with the amino, carboxyl or thiol group of the immunologically active substance, such as those capable of producing a cross linkage between the thiol group and the thiol group, or between the amino group and the thiol group. Examples of suitable compounds which can crosslink between the amino group and the amino group are aliphatic diadehydes (such as glyoxal, malonaldehyde, succinaldehyde, glutaraldehyde) and dichlorotriazines (such as 2-amino-4,6-dichloro-s-triazine), and the like. Suitable croslinking agents between the thiol group and the thiol group are, for, instance, dimaleimide compounds (such as N,N'-o-phenylenedimaleimide, N,N'-m-phenylenedimaleimide). Suitable crosslinking agents between the amino group and the thiol group are exemplified by maleimidocarboxyl-N-hydroxy-succinimide esters (such as m-maleimidobenzoyl-N-hydroxysuccinimide ester, 4-(maleimidomethyl)cyclohexane-1-carboxyl-N-hydroxysuccinimide ester).

In producing the conjugates of this invention by chemical methods, there are two modes:
(1) binding the immunologically active substance to the frosted glass surface through the silane coupling agent, and
(2) binding the immunologically active substance to the frosted glass surface through the silane coupling agent and the crosslinking agent.

According to the first mode, the conjugate can be produced, for example, by the following procedure: the silane coupling agent is firstly bound to the frosted glass by treating the latter with the silane coupling agent so as to make the agent react with the silanol group of the frosted glass surface, and the resulting intermediate product is then reacted with the immunologically active substance to form a linkage between the immunologically active substance and the frosted glass via the silane coupling agent. When an amino-containing silane coupling agent is used, it forms a peptide bond with the carboxyl group of the immunologically active substance. The use of a carboxyl-containing silane coupling agent leads to formation of a peptide bond with the amino group of the immunologically active substances, the use of an epoxy-containing silane coupling agent causes an addition reaction with the amino, carboxyl or thiol group of the immunologically active substance, the use of a thiol-containing silane coupling agent leads to formation of an S—S linkage with the thiol group of the immunologically active substance, the use of a haloalkyl-containing silane coupling agent causes an electrophilic substitution reaction on the amino or thiol group of the immunologically active substance, and the use of an aldehyde-containing silane coupling agent leads to formation of a thioacetal or hemithioacetal with the thiol group of the immunologically active substance. From the viewpoint of firm and permanent bonding of the immunologically active substance and the frosted glass, silane coupling agents which contain an amino group and an alkoxysily group combinedly or a carboxyl group and an alkoxysilyl group combinedly are preferred. The reaction generally occurring between the above silane couping agent and the immunologically active substance is a peptide formation reaction, and it is preferable to use on that occasion a water soluble carbodiimide serving as dehydrating condensation agent, such as N-ethyl-N'-dimethylaminocarbodiimide, 1-ethyl-3-diisopropylaminocarbodiimide or 1-cyclohexyl-3-(2-morpholinoethyl)-carbodiimide.

According to the second mode, the conjugate can be produced, for example, by the following procedure: firstly the silane couping agents is bound to the frosted glass, then the silane-glass reaction product is reacted with the crosslinking agent, and finally the resulting intermediate is reacted with the immunologically active substance. Judging from the view-point of firm and permanent binding of the immunologically active substance with the frosted glass, preferred silane coupling agents are amino- and alkoxysilyl-containing silane coupling agents, especially aminoalkyl-trialkoxysilanes, and preferred crosslinking agents are aliphatic dialdehydes, especially glutaraldehyde.

The amount of the silane coupling agent to be used in the chemical methods is not critical and can vary widely within the scope of this invention. The weight ratio of a solution of the silane coupling agent/the frosted glass can be, for example, 30/100–1000/100, the solution having a concentration of usually 0.01 to 50 vol. % preferably 0.1 to 10 vol. %.

The amount of the crosslinking agent used in the second mode is not critical and can vary widely. The weight ratio of a solution of the crosslinking agent/the frosted glass can be, for example, 30/100–1000/100, the solution having a concentration of usually 0.0001 to 50 wt. %, preferably 0.1 to 20 wt. %.

Procedures of binding the immunologically active substance to the frosted glass by the aid of the silane coupling agent and if necessary the crosslinking agent may be similar to those known so far, except that the frosted glass is used as carrier glass.

Thus, an illustrative example of such procedures, wherein the immunologically active substance is bound to the frosted glass surface via the silane coupling agent according to the first mode, is as follows. The frosted glass is well immersed in a solution of the silane coupling agent having a concentration of 0.01 to 50 V/V % (preferably 0.1 to 10 V/V %) in an organic solvent (such as acetone or toluene) at a temperature of 0° to 80° C. for 10 minutes to 24 hours, to allow the silane coupling agent to react with the frosted glass. The so-treated frosted glass is separated from the reaction mixture, and washed thoroughly in sequence with methanol and deionized water. To this frosted glass is added 10 to 1000 parts (preferably 50 to 300 parts) of a solution of the immunologically active substance having a concentration of 0.001 to 40 g/100 ml (preferably 0.01 to 0.1 g/100 ml) per 100 parts of the frosted glass, and the reaction is allowed to proceed at about 0° to 40° C. for 10 minutes to 24 hours (preferably for 1 to 3 hours) so that the frosted glass and the immunologically active substance may be bound together through the silane coupling agent. It is preferable to use a solution of a water-soluble carbodiimide at a concentration of 0.1 to 10 g/100 ml on the occasion of reacting the immunologically active substance with the frosted glass to which an amino- or carboxyl-containing silane coupling agent has been bound.

An illustrative examples of procedures, wherein the immunologically active substance is to be bound to the frosted glass surface with the aid of the silane coupling agent and the crosslinking agent in accordance with the second mode, is as follows. The frosted glass is well immersed in a solution of the silane coupling agent having a concentration of 0.01 to 50 V/V % (preferably 0.1 to 10 V/V %) in an organic solvent (such as acetone or toluene) at a temperature of 0° to 80° C. for 10 minutes to 24 hours so that the silane coupling agent may react with and be bound to the frosted glass. Then the so-treated frosted glass is separated from the reaction mixture, and washed thoroughly in sequence with methanol and deionized water. This frosted glass is then well immersed in an aqueous solution of the crosslinking agent having a concentration of 0.0001 to 50 W/W % (preferably 0.1 to 20 W/W %) at about 0° to 40° C. for 30 minutes to 10 hours, whereby the crosslinking agent is bound to the silane coupling agent that has been bound to the frosted glass. The frosted glass so treated is separated from the reaction mixture and washed thoroughly with deionized water. To the frosted glass is added 10 to 1000 parts (preferably 50 to 300 parts) of a solution of the immunologically active substance having a concentration of 0.001 to 40 g/100 ml (preferably 0.01 to 0.1 g/100 ml) per 100 parts of the frosted glass, and the reaction is allowed to proceed at about 0° to 40° C. for 10 minutes to 24 hours (preferably for 1 to 3 hours), whereby the immunologically active substance is bound to the frosted glass through the silane coupling agent and the crosslinking agent.

The immunologically active substance-glass conjugates obtained according to this invention can contain usually 0.1 to 1000 $\mu$g, preferably 50 to 500 $\mu$g (per g. of the frosted glass) of the immunologically active substance bound to the glass. The amount of the silane coupling agent bound to the frosted glass in the chemical method may be, for example, $10^{-5}$ to $1\mu$ mole (preferably $10^{-4}$ to $10^{-2}\mu$ mole) per g. of the glass. The amount of the crosslinking agent bound to the conjugate in the second mode is preferably stoichiometric amount to the crosslink the functional group of the silane coupling agent with the functional group of the immunologically active substance, but, may vary, for example, from 20% to 100% of the stoichiometric amount.

The immunologically active substance-frosted glass conjugated prepared in this manner are stable and can be stored for more than one year in a 0.01 M phosphate buffered physiological saline solution (pH7.2) containing 1% sodium nitride and 1% bovine serum albumin at 4° C., for instance.

The immunologically active substance-frosted glass conjugates of the invention can be used as diagnostic reagents for assaying physiologically active substances in body fluids such as urine and serum. Examples of such physiologically active substances assayable with the conjugates include hormones, such as insulin, gonadotropin, 17-ketosteroids, growth hormone, thyroxine, triiodothyronine and thyroid stimulating hormone; proteins, such as IgA, IgG, IgE, IgM, $\alpha$-fetoprotein, CEA and protamines; antigenic elements or fractions of pathogenic bacteria, viruses and protozoa, such as streptococci, hepatitis virus, rubella virus, *Toxoplasma gondii* and malarial parsites; and antibodies against bacteria, viruses, protozoa, medicines and so on.

The immunologically active substance-frosted glass conjugates of the present invention may be used for assaying physiologically active substance in body fluids in accordance with conventional methods of RIA or EIA using solid systems. Typical of such methods are:

(1) Competitive reaction method, which comprises reacting a substance to be assayed and certain amount of an enzyme- or isotope-labeled immunologically active substance (said substance being the same as the substance to be assayed) competitively with an immunologically active substance-frosted glass conjugate wherein an antigen or antibody against the substance to be assayed is bound to a frosted glass, then determining the enzyme activity or radioactivity of the substance that has either been bound or not been bound to the immunologically active substance-frosted glass conjugate, and comparing the result of the determination with the results obtained by the same procedure using known amounts of the same substance as the one to be assayed, to obtain an assay result;

(2) sandwich method, which comprises reacting a substance to be assayed with an immunologically active substance-frosted glass conjugate wherein an antigen or antibody against the substance to be assayed is bound to a frosted glass, further reacting the bound substance with an immunologically active substance (antigen or antibody against the substance to be assayed) labeled with an enxyme or an isotope, then determining the enzyme activity or radioactivity of the substance that has been bound to the immunologically active substance-frosted glass conjugate, and comparing the result of the determination with the results obtained by the same procedure using known amounts of the same substance as the one to be assayed, to obtain an assay result; and (3) a method which comprises reacting a substance to be assayed and a certain amount of an enzyme- or isotope-labeled immunologically active substance (said substance being originally the same as the one to be assayed) competitively with an antigen or antibody against the substance to be assayed, further reacting the bound antigen or antibody with an immunologically active substance-frosted glass conjugate wherein an antibody against said antigen or said antibody is bound to a frosted glass, then determining the enzyme activity or radioactivity of the substance that has either been bound or not been bound to the immunologically active substance-frosted glass conjugate, and comparing the result of the determination with the results obtained by the same procedure using known amounts of the same substance as the one to be assayed, to derive an assay data.

Naturally, the methods of applying the conjugates of the invention are not limited to those mentioned above.

The immunologically active substance-frosted glass conjugates of the present invention can be used in place of various known insolubilized immunologically active substances in EIA and RIA. Thus, the conjugates of the invention can be used, for example, in place of:

(1) the polystyrene tube-bound anti-CEA in the method described by S. Hammarström) et al. in Proc. Nat. Acad. Sci. U.S.A. 72,1528 (1975); (2) the cellulose-bound anti-rabbit $\gamma$G or the cellulose-bound anti-HCG in the method described by B. K. van Weeman et al. in FEBS Letters 15, 232 (1971); (3) the polystyrene tube-bound anti-AFP in the method described by L. Belanger et al. in Clin. Chim. Acta 48,15 (1973); (4) the polystyrene hemagglutination plate-bound anti-HBs in the method described by G. Wolters et al. In J. Clin. Path.

29,873 (1976); (5) the polystyrene tube-bound anti-IgE in the method described by D. R. Hoffman in J. Allergy Clin. Immunol. 51,303 (1973); (6) the dextran-bound anti-insulin in the method described by K. Kato et al. in J. Biochem. 78, 235 (1975); (7) the polystyrene tube-bound specific antibody in the method described by S. E. Salmon in J. Immunol. 103, 129 (1969); and (8) the poly(tetrafluoroethylene-g-isothiocyanatostyrene) disc-bound anti-human growth hormone in the method described by K. Catt in J. Lab. Clin. Med. 70,820 (1970).

The immunologically active substance-frosted glass conjugates of the invention contain large amounts of the immunologically active substances that are bound firmly and stably, and, when used as insolubilized immunologically active substances, provide very high sensitivity and assay precision as well as a broad assay range and further advantages that they can be stored for a prolonged period of time and handled very easily in assaying, and that they can be easily produced commercially. Thus they are very useful in the field of diagnostic medicine.

In addition, the immunologically active substance-frosted glass conjugates of this invention give rise to little adsorption of assay reagents, dyes or pigments and substances in body fluids, which cause interference in assaying and hinder the activity of the conjugates; and therefore show far better precision in assay (especially in EIA), as compared with porous glass-bound immunologically active substance conjugates, which lead to adsorption of larger amounts of such interfering substances. Moreover, the immunologically active substance-frosted glass conjugates of the invention having relatively larger sizes (the maxmum diameter of usually 1 to 20 mm and the minimum diameter of usually 1 mm or more) can be easily handled in assay, (for instance, they can be put into or taken out from test tubes with tweegers); while the porous glass-bound conjugates, which are generally very minute, are troublesome to handle.

Having generally described the invention, a more complete understanding can be obtained by reference to certain specific examples, which are included for purposes of illustration only and are not intended to be limiting unless otherwise specified.

The frosted glasses used in the following examples are as follows:

(1) Frosted glass I (frosted glass beads by physical method)

Three hundred glass beads (6 mm in diameter) were sandblasted by forcibly spraying 60-mesh emery (abrasive material) onto the glass beads under an air pressure of 5 kg/cm$^2$ for 15 minutes. Then the emery adhereing to the glass beads was washed away to obtain frosted beads having uniformly frosted surfaces and having a frosting-degree of 4.5 determined by the following method.

Measurement of the frosting-degree of the frosted glass 50 pieces of the frosted glass beads and 50 pieces of the unfrosted glass beads (having the same shape and size as those of the frosted glass beads) were immersed in 25 ml of 10% solution of γ-aminopropyl-triethoxysilane in acetone. After incubation at 25° C. for an hour, these beads were filtered off and washed sufficiently with deionized water. Then, 100 pieces (total) of these glass beads were immersed in 25 ml of 20% aqueous solution of glutaraldehyde. After incubation at 25° C. for an hour, these treated beads were washed thoroughly with deionized water. The glass beads so treated were then immersed in 25 ml of an aqueous solution containing 12.5 mg of glucose oxidaze (GOD) (Enzyme activity of 34.0 U/ml). After incubation at 25° C. for an hour and then at 4° C. for 15 hours, these beads were washed with deionized water to obtain a GOD-frosted glass bead conjugate and a GOD-unfrosted glass bead conjugate. In each of ten test tubes, one bead of the GOD-frosted glass bead conjugate was placed. In each of other ten test tubes, one bead of GOD-unfrosted glass bead conjugate was placed. Into each of these twenty test tubes, 2 ml of deionized water was added, the content was stirred using a mixer, and the supernatant liquid was sucked off using an aspirator. This washing procedure was repeated twice. Then, 0.3 ml of 0.01 M sodium acetate buffer solution (pH 5.1), 2.0 ml of MBTH-DEA solution (10 mg of sodium ethylenediaminetetraacetate, 1.7 mg of 3-methyl-benzothiazolinonehydrazone hydrochloride, 0.004 ml of N,N-diethylaniline in 100 ml of 0.1 M acetic acid aqueous solution) and 0.5 ml of peroxidase (POD) solution (60U of POD in 1 ml of 0.1 M sodium acetate aqueous solution) were added into each test tube. After pre-incubation at 37° C. for 5 minutes, 0.5 ml of 15 g/100 ml solution of β-D-glucose in 0.1 M acetic acid solution was added into each test tube. After incubation under shaking at 37° C. for 6 minutes exactly, 1 ml of 0.5 N hydrochloric acid was added into each test tube to stop the reaction. Absorbance at 590 nm of the resulting supernatant liquid in each test tube was measured. The frosting-degree was calculated according to the equation (1), using the average of absorbances of the ten supernatant liquids of the GOD-frosted glass conjugate and that of the GOD-unfrosted glass conjugate as the enzyme activities.

(2) Frosted glass II (frosted glass tubes by chemical method)

One hundred small glass tubes (6 mm in outer diameter, 4 mm in inner diameter and 10 mm in length) were immersed in 200 ml of a frosting solution containing 2% hydrofluoric acid and 1% ammonium fluoride at room temperature for an hour. Then the glass tubes were taken out and washed with water, to obtain frosted glass tubes having uniformly frosted surfaces and having a frosting-degree of 3.2 determined by similar method as in the above (I).

EXAMPLE 1

Preparation of an immunologically active substance-frosted glass conjugate

The one hundred frosted glass tubes (frosted glass II) were immersed in 100 ml of 0.5% solution of γ-aminopropyl-triethoxysilane in acetone. After incubation at room temperature for 10 hours, the tubes were filtered off and washed with methanol and then with water. These 100 frosted glass tubes to which the amino-containing silane coupling agent had been bound were immersed in 40 ml of normal saline solution. A solution of 50 mg of human IgG in 10 ml of physiological saline solution and a solution containing 0.2% N-ethyl-N'-dimethylaminopropylcarbodiimide in 10 ml of physiological saline solution were added thereto. After treatment under immersion at 37° C. for 2 hours, the tubes were washed in sequence with water, 1 M propionic acid aqueous solution and water, until no protein was detected in the washings any more. Thus, there was obtained a conjugate having a bound protein content of 63 μg per gram of the glass, determined as follows.

Measurement of the bound protein content

According to the method described by S. Moore et al. in Methods in Enzymology 6. 819 (1963), 10 pieces of the protein-glass conjugate were immersed in a solution of 6 N hydrochloric acid; and the whole system was sealed under reduced pressure, and then heated at 110° C. for 30 hours. The protein content was measured by ninhydrin coloration.

EXAMPLE 2

Preparation of an immunologically active substance-frosted glass conjugate

Two hundred of the frosted glass beads (frosted glass I) were immersed in 100 ml of 0.5% solution of γ-aminopropyl-triethoxysilane in toluene and boiled for 7 hours. The beads were then filtered off and washed with methanol and then with water. To the 200 frosted glass beads to which the aminocontaining silane coupling agent had been bound, there was added 100 ml of 2% glutaraldehyde aqueous solution. After standing for 2 hours at 4° C., the beads were washed with deionized water 4 to 6 times until they did not carry the odor of glutaraldehyde any more. The 200 frosted glass beads so treated were then immersed in 40 ml of normal saline solution. Thereto was added a solution of 50 mg of anti-human-insulin (rabbit) in 10 ml of physiological saline. After allowing the reaction to proceed at 30° C. for 2 hours, the glass beads were thoroughly washed with water until no protein was detected in the washings any more.

Thus, there was obtained a conjugate having a bound protein content of 148 μg per gram of the glass, as measured similarly as in Example 1.

EXAMPLE 3

Assay of an immunologically active substance (human insulin) with the immunologically active substance-frosted glass conjugate (Sandwich EIA)

Assay of insulin by the samdwich EIA method was carried out using the anti human insulin (rabbit)-frosted glass bead conjugates prepared in Example 2. Thus, 0.3 ml of a solution of 0.01 M sodium phosphate buffer (pH 7.3) containing 0.85% sodium chloride and 0.1% bovine serum albumin (such solution being called "buffer solution A" hereinafter) were placed in each of test tubes (0.9×10 cm).

One of the anti human insulin-frosted glass conjugate beads prepared in Example 2 was put into each test tube. Various dilutions of human insulin were prepared with buffer solution A and added into the test tubes (0.1 ml/tube). After shaking at room temperature for an hour, 0.1 ml of phosphatase-labeled anti human insulin was added into each test tube. After further shaking or incubation for an hour, about 5 ml of normal saline solution was added into each test tube, the content was stirred using a mixer, and the supernatant liquid was sucked off using an aspirator. This washing procedure was repeated four times. Then, 2 ml of an enzyme substrate reagent (contained in an ALP assay kit, Chugai Pharmaceutical Co., Ltd.) was added into each test tube. Incubation or reaction at 37° C. for 30 minutes with shaking followed. Then 2.0 ml of a color former solution (contained in said ALP assay kit, Chugai Pharmaceutical Co., Ltd.) was added into each test tube. After additional incubation with shaking at 37° C. for 30 minutes, the absorbance at 570 nm was measured so as to determine the enzyme activity. FIG. 1 is the standard assay curve for human insulin when the rabbit anti human insulin-frosted glass bead conjugate is used.

EXAMPLE 4

Performance evaluation of the immunologically active substance-frosted glass conjugate-1

A rabbit anti-human insulin-unfrosted glass bead conjugate was prepared in accordance with Example 2 but using unfrosted glass beads(6 mm in diameter), and compared with the rabbit anti-human insulin-frosted glass bead conjugate prepared in Example 2 with regard to the amount of bound protein. The bound protein was determined according to the method described in Example 1. The results are shown in Table 1.

TABLE 1

| Sample | Bound protein (μg/g of glass beads) |
|---|---|
| Rabbit anti human insulin-frosted glass bead conjugate | 148 |
| Rabbit anti human insulin-unfrosted glass bead conjugate | 32 |

As can be seen from Table 1, a larger amount of immunologically active substance can be bound to frosted glass bead than to unfrosted glass bead.

EXAMPLE 5

Performance evaluation of the immunologically active substance-frosted glass conjugate-2

A rabbit anti human insulin-unfrosted glass bead conjugate was prepared according to Example 2 except that unfrosted glass beads were used. Using this cojugate and the rabbit anti human insulin-frosted glass bead conjugate prepared in Example 2, determination of human insulin was made according to the method described in Example 3, and the sensitivity, assay range and precision were compared between both the conjugates. The results are shown in Table 2.

TABLE 2

| | Assay of human insulin with rabbit anti human insulin-frosted glass bead conjugate | Assay of human insulin with rabbit anti human insulin-unfrosted glass bead conjugate |
|---|---|---|
| Sensitivity (μU/ml) | 0.2 | 20 |
| Assay range (μU/ml) | 0.2-450 | 20-250 |
| Precision when 120 μU/ml human insulin was assayed | 118 ± 5 μU/ml (Coefficient of variation = 4.2%) | 110 ± 20 μU/ml (Coefficient of variation = 27.3%) |

As can be seen from Table 2, the immunologically active substance frosted glass bead conjugate prepared from frosted glass bead is far better in sensitivity and assay range as well as in assay precision than the one prepared from unfrosted glass bead

EXAMPLE 6

Preparation of an immunologically active substance-frosted glass conjugate (1) Reduction of anti human α-fetoprotein (anti human AFP)

[To 10 ml aqueous solution of 100 mg of anti human AFP (rabbit) (DAKO-Immunoglobulins Ltd., Denmark) was added 1 ml of 0.1 M aqueous solution of 2-mercaptoethylamine], and incubation was effected at 37° C. for 90 minutes. The so-reduced anti human AFP was separated and purified through a Sephadex G-25 column (1×40 cm) bufferized with 0.1 M sodium acetate buffer (pH 5.0).

(2) Preparation of immunologically active substance (anti human AFP)frosted glass bead conjugate 200 pieces of the frosted glass beads (frosted glass I) were immersed in 100 ml of 0.5% γmercaptopropyltrimethoxysilane solution in toluene, and the reaction was allowed to proceed under reflux for 8 hours. The beads were then filtered off, and washed with methanol and then with water. To the 200 frosted glass beads to which the thiol-containing silane coupling agent had been bound, there was added 100 ml of a saturated N,N'-o-phenylenedimaleimide solution in 0.1 M sodium acetate buffer (pH 5.0). Incubation was effected at 30° C. for 2 hours. The beads were washed 4 times with deionized water. The 200 beads so treated were then immersed in 90 ml of 0.1 M sodium acetate buffer (pH 5.0), and 50 mg of the reduced anti human AFP prepared in the above (1) in 10 ml of 0.1 M sodium acetate buffer (pH 5.0) was added. After the subsequent reaction at 30° C. for 2 hours, the frosted glass beads were washed thoroughly with water until no protein was detected in the washings any more.

There was obtained an anti human AFP-frosted glass conjugate having a bound protein content of 103 μg per gram of the glass, determined by similar method as in Example 1.

COMPARATIVE EXAMPLE 1

Following the procedure of Example 6 but using untreated (unfrosted) glass beads (6 mm in diameter), there was obtained an anti human AFP-unfrosted glass bead conjugate having a bound protein of 19 μg per gram of the glass determined by the method described in Example 1.

EXAMPLE 7

Assay of a physiologically active substance (human α-fetoprotein—human AFP) using the immunologically active substance-glass conjugate by sandwich EIA Using the anti human AFP-frosted glass bead conjugate and the anti human AFP-unfrosted glass bead conjugate, assay of human AFP was carried out according to the sandwich EIA.

Figure 2:
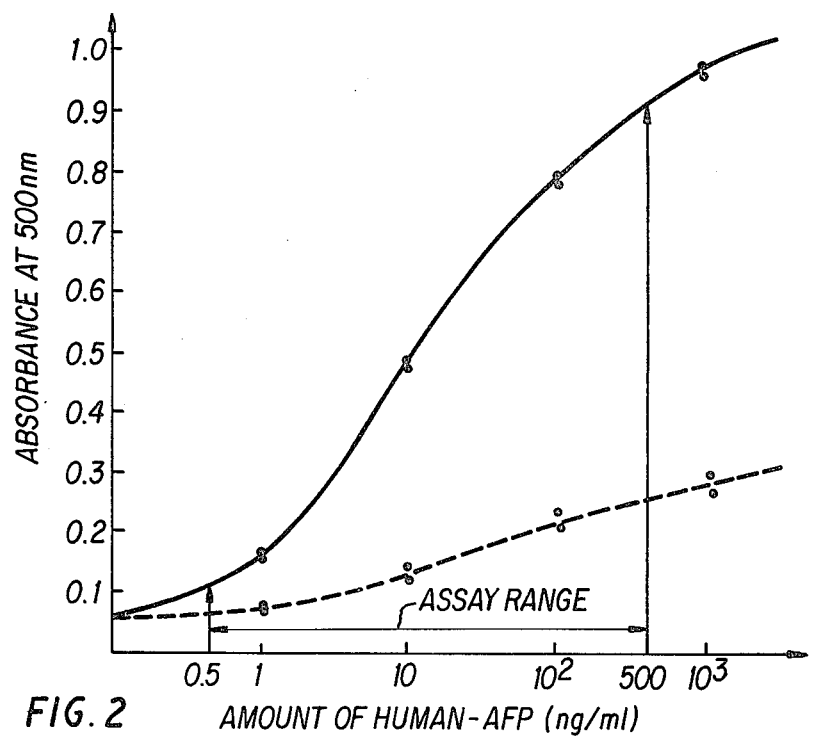
FIG. 2 is a standard curve for assaying human α-fetoprotein by sandwich EIA method (cf. Example 7).

Thus, 0.3 ml of the buffer solution A of Example 3 and one bead of the anti human AFP-frosted glass bead conjugate of Example 6 or the anti human AFP-unfrosted glass bead conjugate of comparative Example 1 were placed in each of test tubes (0.9×10 cm). Various dilutions of human AFP were prepared with the buffer solution A, and 0.1 ml portions thereof were added into each test tube. Incubation was effected at room temperature for an hour. After the reaction, about 5 ml of physiological saline solution was added, the mixture was stirred using a mixer, and the supernatant liquid was sucked off using an aspirator to effect whashing of the bead. Then 0.1 ml of a peroxidase labeled anti human AFP and 0.3 ml of the buffer solution A were added into each test tube and incubation was effected at room temperature for an hour. After the reaction, about 5 ml of physiological saline solution was added, the mixture was stirred using a mixer, and the supernatant liquid was sucked off using an aspirator to effect washing of the bead. Enzyme substrate reagents [2.5 ml of a freshly prepared solution of 5-aminosalicylic acid (0.6 mg/ml) and urea peroxide (0.2 mg/ml) in 0.03 M sodium phosphate buffer (pH 6.0)] were added into each test tube. After an hour of incubation at 37° C., 0.1 ml of 10% aqueous solution of sodium azide was added to each test tube to discontinue the reaction, and the absorbance at 500 nm was measured and related to the enzyme activity. The standard assay curve for human AFP when the anti human AFP-frosted glass bead conjugate was used and that when the anti human AFP-unfrosted glass bead conjugate was used were as shown in FIG. 2 by the solid line and the broken line, respectively.

Both the conjugates were compared in respect of sensitivity, assay range and precision. The results are shown in Table 3.

TABLE 3

| | Assay of human AFP with anti human AFP-frosted glass bead conjugate bead | Assay of human AFP with anti human AFP-unfrosted glass bead conjugate |
|---|---|---|
| Sensitivity (ng/ml) | 0.5 | 10 |
| Assay range (ng/ml) | 0.5–500 | 10–100 |
| Precision (when 80 ng/ml human AFP was assayed) | 79 ± 3 ng/ml (Coefficient of variation = 3.8%) | 76 ± 28 ng/ml (Coefficient of variation = 36.8%) |

It is clear from FIG. 2 and Table 3 that the immunologically active substance-frosted glass conjugate prepared by using the frosted glass bead is far better in sensitivity, assay range and precision than the one prepared by using untreated glass beads.

What is claimed as new and desired to be secured by Letters Patent is:

1. An immunologically active substance-glass conjugate which comprises an immunologically active substance bound to a frosted glass.

2. The conjugate of claim 1, which has a minimum diameter of at least 1 mm.

3. The conjugate of claim 1, wherein the immunologically active substance and the frosted glass are bound together with the aid of a silane coupling agent with or without a crosslinking agent.

4. The conjugate of claim 3, wherein the silane coupling agent has both a functional group reactive with the frosted glass and a functional group reactive with the immunologically active substance, the crosslinking agent, or both.

5. The conjugate of claim 3, wherein the silane coupling agent has both a functional group reactive with a silanol group and a functional group reactive with an amino, carboxyl or thiol group.

6. The conjugate of claim 5, wherein the functional group reactive with a silianol group is an alkoxysilyl or halosilyl group.

7. The conjugate of claim 5, wherein the functional group reactive with an amino, carboxyl or thiol group is a carboxyl, epoxy, haloalkyl, aldehyde, amino, thiol, isocyanate, carboxylate, imino or nitrile group.

8. The conjugate of claim 5, wherein the functional group reactive with the amino group is a carboxyl, epoxy, haloalkyl or aldehyde group.

9. The conjugate of claim 5, wherein the functional group reactive with a carboxyl group is an amino or epoxy group.

10. The conjugate of claim 5, wherein the functional group reactive with a thiol group is a thiol, epoxy, haloalkyl or aldehyde group.

11. The conjugate of claim 3, wherein the silane coupling agent is an alkoxysilyl group-containing silane coupling agent having an amino, thiol, epoxy, carboxyl or haloalkyl group.

12. The conjugate of claim 3, wherein the crosslinking agent is a compound which can crosslink the silane coupling agent and the immunologically active substance.

13. The conjugate of claim 3, wherein the crosslinking agent is a compound which can crosslink between an amino, carboxyl or thiol group of the silane coupling agent and an amino, carboxyl or thiol group of the immunologically active substance.

14. The conjugate of claim 3, wherein the crosslinking agent is a compound which can crosslink between amino groups, a compound which can crosslink between thiol groups or a compound which can crosslink between an amino group and a thiol group.

15. The conjugate of claim 14, wherein the compound which can crosslink between amino groups is an aliphatic dialdehyde or a dichlorotriazine.

16. The conjugate of claim 14, wherein the compound which can crosslink between thiol groups is a dimaleimide compound.

17. The conjugate of claim 14, wherein the compound which can crosslink between an amino group and a thiol group is a maleimidocarboxyl-N-hydroxysuccinimide ester.

18. The conjugate of claim 1, wherein the immunologically active substance is an antigen.

19. The conjugate of claim 18, wherein the antigen is a hormone, a protein, or an antigenic component of a pathogen.

20. The conjugate of claim 19, wherein the antigenic component of a pathogen is a pathogenic bacterium, virus or protozoon.

21. The conjugate of claim 1, wherein the immunologically active substance is an antibody.

22. The conjugate of claim 21, wherein the antibody is an antiserum obtained by immunizing a mammal with an antigen.

23. The conjugate of claim 1, wherein the frosted glass is a physically frosted glass.

24. The conjugate of claim 23, wherein the physically frosted glass is a glass abraded with an abrasive material.

25. The conjugate of claim 1, wherein the frosted glass is a chemically frosted glass.

26. The conjugate of claim 25, wherein the chemically frosted glass is a glass frosted by treatment with a frosting agent containing hydrofluoric acid, ammonium fluoride or an alkali.

27. The conjugate of claim 1, wherein the frosted glass has a shape of cylindrical, spherical, cubic or tubular glass body.

28. The conjugate of claim 1, wherein the frosted glass comprises a glass body having the maximum diameter of 1 to 20 mm and the minimum diameter of 1 mm or more.

29. The conjugate of claim 1, wherein the frosted glass has a frosting- degree of 1.5 to 10.0.

30. A process for producing an immunologically active substance-glass conjugate, which comprises reacting an immunologically active substance and a frosted glass with a silane coupling agent with or without a crosslinking agent.

31. The process of claim 30, which comprises reacting a frosted glass with a silane coupling agent, and then reacting the resulting product with an immunologically active substance, with or without a crosslinking agent.

32. A process for immobilizing an immunologically active substance which comprises reacting an immunologically active substance with silane coupling agent-treated frosted glass, with or without a crosslinking agent.

33. In a process for assaying a physiologically active substance in a body fluid by using a solid phase system, the improvement which comprises using as the solid phase system an immunologically active substance-glass conjugate comprising an immunologically active substance bound to a frosted glass.

34. The process of claim 33, wherein assaying is carried out by enzyme-immunoassay or by radioimmunoassay.

35. The process of claim 33, wherein assaying is carried out by enzyme-immunoassay method.

* * * * *